(12) United States Patent
Gordon

(10) Patent No.: US 7,987,810 B1
(45) Date of Patent: Aug. 2, 2011

(54) ARTICULATING PAPER DISPENSER

(76) Inventor: Karen Gordon, Hollywood, FL (US)

( * ) Notice: Subject to any disclaimer, the term of this patent is extended or adjusted under 35 U.S.C. 154(b) by 750 days.

(21) Appl. No.: 11/769,139

(22) Filed: Jun. 27, 2007

Related U.S. Application Data

(60) Provisional application No. 60/817,024, filed on Jun. 28, 2006.

(51) Int. Cl.
B05C 3/00 (2006.01)
(52) U.S. Cl. ......... 118/404; 118/400; 118/419; 118/423
(58) Field of Classification Search .................. 118/400, 118/DIG. 17, 404, 419, 423; 242/320, 588, 242/588.3, 588.6, 905, 579, 580
See application file for complete search history.

(56) References Cited

U.S. PATENT DOCUMENTS

| | | | | |
|---|---|---|---|---|
| 2,443,971 A | * | 6/1948 | Winzer | ............................ 118/43 |
| 3,959,881 A | | 6/1976 | Kokal, Jr. | |
| 5,181,849 A | | 1/1993 | Callne | |
| 5,242,495 A | * | 9/1993 | Hammond et al. | ............. 118/43 |
| 5,249,547 A | * | 10/1993 | Takada et al. | ................. 118/415 |
| 5,672,206 A | | 9/1997 | Gorman | |
| 5,829,278 A | * | 11/1998 | Koo | ............................ 68/205 R |
| 5,941,150 A | | 8/1999 | Kropf et al. | |
| 5,951,762 A | * | 9/1999 | Shangold et al. | ............. 118/405 |
| 6,343,491 B1 | * | 2/2002 | Jung | ............................. 68/13 R |
| 6,497,345 B1 | | 12/2002 | Wilker et al. | |
| 6,503,326 B1 | * | 1/2003 | Mikelionis | .................... 118/419 |
| 6,547,881 B1 | | 4/2003 | Klockner | |
| 6,820,785 B2 | * | 11/2004 | Kapiloff | .......................... 225/14 |
| 6,932,602 B2 | | 8/2005 | Hamilton et al. | |
| 7,018,473 B2 | * | 3/2006 | Shadrach, III | ................ 118/315 |

* cited by examiner

Primary Examiner — Dah-Wei D. Yuan
Assistant Examiner — Charles J Capozzi
(74) Attorney, Agent, or Firm — Gold & Rizvi, P.A.; Glenn E. Gold; H. John Rivzi

(57) ABSTRACT

An articulating paper dispenser is provided including an upper housing and a lower housing that, when engaged together, form a both a lubricant container and a chamber for containing an articulating paper roll. The articulating paper that is unwound from the articulating paper roll is passed through the lubricant container. The articulating paper dispenser will preferably include pressure rollers to guide the articulating paper through a dispensing slot in the dispenser. The lubricant container is configured to contain a lubricant that increases the marking ability of the articulating paper. As the articulating paper is dispensed from the articulating paper system, it is coated on both sides with a thin layer of the lubricant. The lubricant-coated articulating paper is then used to check a patient's occlusion more accurately and precisely.

19 Claims, 5 Drawing Sheets

ARTICULATING PAPER DISPENSER

CROSS-REFERENCE TO RELATED APPLICATION

This application claims the benefit of co-pending U.S. Provisional Patent Application Ser. No. 60/817,024, Jun. 28, 2006, which is incorporated herein in its entirety.

BACKGROUND OF THE INVENTION

1. Field of the Invention

The present invention relates generally to dental devices, and more particularly, to a device to dispense articulating paper in a manner that improves the articulating paper's ability to indicate dental occlusion or alignment of a patient's teeth by transfer of material to teeth.

2. Description of the Prior Art

It is important in many dental procedures to determine the dental occlusal contact points, the points where the teeth of the lower jaw contact the corresponding teeth of the upper jaw when the jaws are closed. These dental procedures include not only procedures in which the occlusal surface of the dental restorative or of the natural tooth is contoured, such as in preparing dental restoratives of various types or in improving the occlusion of certain or all of the natural teeth, but also include analyzing the progress of dental treatments or orthodontic treatment plans.

Typically the patient's occlusion is determined by conducting dental articulation tests using articulating paper. Articulating paper is formed from varying materials such as paper, Mylar, film, or silk, which is embedded, impregnated, or coated with one or more color pigments. Articulating paper is commonly available in strips or rolls of varying thicknesses.

The articulating paper is placed between the occlusal surfaces of the upper and lower teeth of the patient. Then the opposing tooth surfaces are brought into occluding relationship with each other, which causes the color pigment of the articulating paper to be displaced onto the tooth surfaces at the points of contact. The articulating paper is removed, and the markings remaining on the teeth are analyzed to determine the points of contact as well as the relative biting pressures exerted by the occlusal surfaces of the upper and lower teeth.

The size, shape, and/or color of the displaced color pigment is indicative of such contact points and pressures. Thus the occlusal surface of the dental restorative or the natural tooth can be contoured or the progress of the orthodontic treatment ascertained. For example, if the bite surface is too high, a bite plane correction can be made by scraping or filing the marked contact points to the extent necessary to achieve the proper bite contact. Without precise and accurate markings, the dental professional may not have the information required to perform these and other dental procedures in an optimal manner, increasing the risk of dental disease, poor cosmetic results, or patient discomfort.

The current articulating paper system does not consistently provide the required precise, accurate markings. Furthermore, at times the color pigment coating on the paper becomes dry, resulting in indistinct or inaccurate marking of the contact points between the occlusal surfaces. As a solution to this problem, petroleum jelly can be manually spread thinly on the coated sides of each strip of the articulating paper immediately prior to use. While this practice makes the markings bolder and more predictable, it is messy and takes additional chair time. It would thus be beneficial to have a device that could lubricate the articulating paper in a neat, streamlined, and time-efficient manner.

Accordingly, there is an established need for a time-saving articulating paper dispenser that could lubricate the articulating paper neatly, quickly, and efficiently so that the articulating paper would provide more precise, accurate marking of the contact points between the occlusal surfaces.

SUMMARY OF THE INVENTION

The present invention is directed to a convenient and labor-saving articulating paper dispenser that is capable of neatly, quickly, and efficiently coating the articulating paper with a thin layer of lubricant so when the articulating paper is used it provides more precise, accurate, and predictably markings of the dental occlusal contact points. The articulating paper dispenser includes a dispenser housing having means to support a web or roll of articulating paper and a lubricant container disposed in the dispenser through which articulating paper is passed before being dispensed.

The articulating paper dispenser will preferably include pressure rollers to guide the articulating paper through a dispensing slot in the dispenser. The lubricant container is configured to contain a lubricant that increases the marking ability of the articulating paper. As the articulating paper is dispensed from the articulating paper system, it is coated on both sides with a thin layer of the lubricant. The lubricant-coated articulating paper is then used to check a patient's occlusion more accurately and precisely.

An object of the present invention is to provide an articulating paper dispenser that is configured to lubricate articulating paper in a neat, tidy, streamlined manner.

Another object of the present invention is to provide an articulating paper dispenser that is configured to save both time and labor.

A further object of the present invention is to provide an articulating paper dispenser that can be adapted for use with a wide variety of articulating papers, including ones formed from an assortment of different materials and ones of differing sizes.

Another object of the present invention is to provide an articulating paper dispenser that is configured to modify the articulating paper by lubrication so that the articulating paper is capable of giving precise, accurate markings of the contact points between the occlusal surfaces of teeth.

An additional object of the present invention is to provide an articulating paper dispenser that is cost-effective.

These and other objects, features, and advantages of the present invention will become more readily apparent from the attached drawings and the detailed description of the preferred embodiments, which follow.

BRIEF DESCRIPTION. OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION OF THE PREFERRED EMBODIMENTS

Shown throughout the figures, the present invention is directed toward a convenient and economical articulating paper dispenser that is capable of lubricating articulating paper in an efficient, neat, tidy, and time-efficient manner resulting in more precise, accurate marking of occlusal contact points by the lubricated articulating paper.

Figure 1:
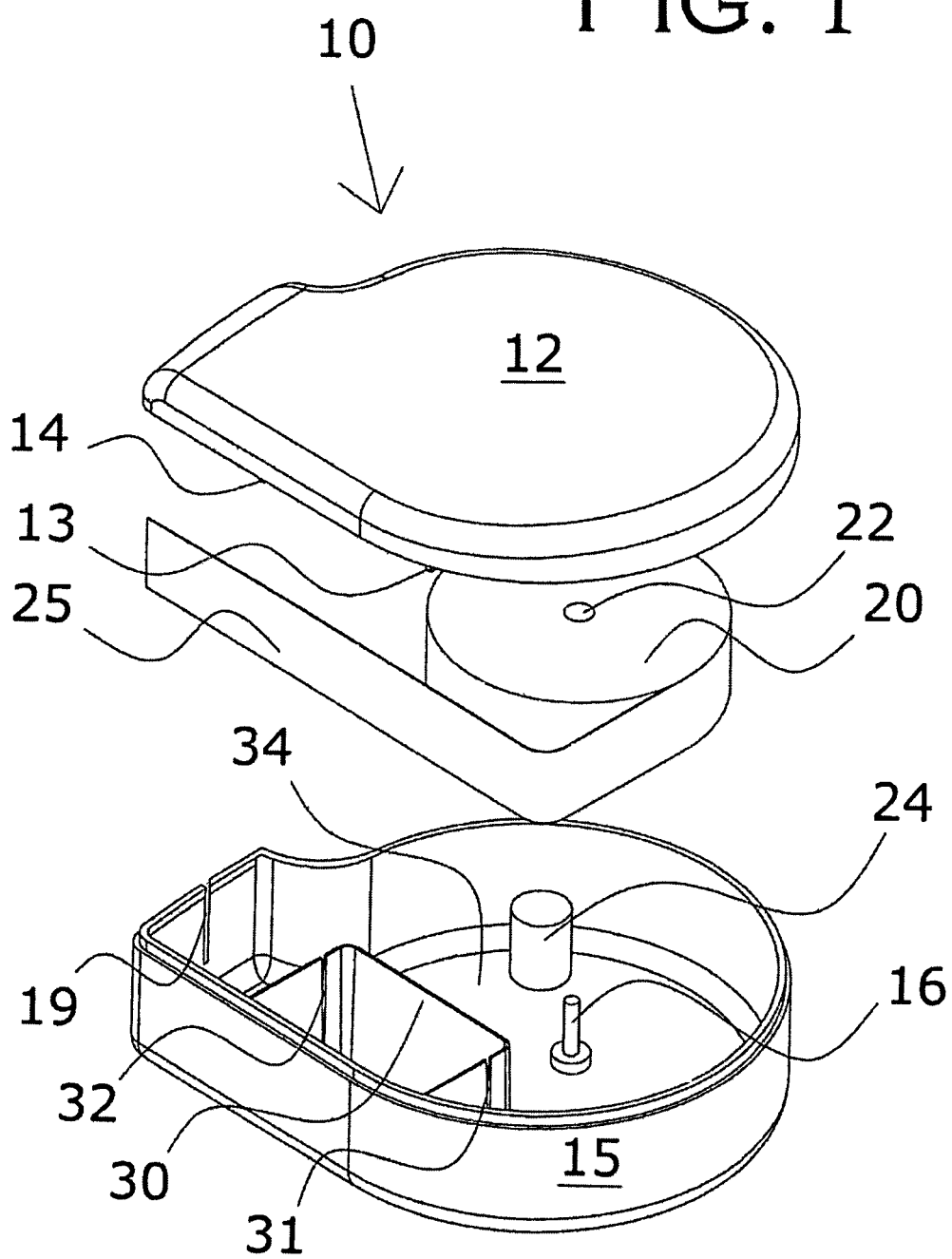
FIG. 1 is a perspective, expanded view showing a first embodiment of the articulating paper dispenser of the present invention.
Figure 2:
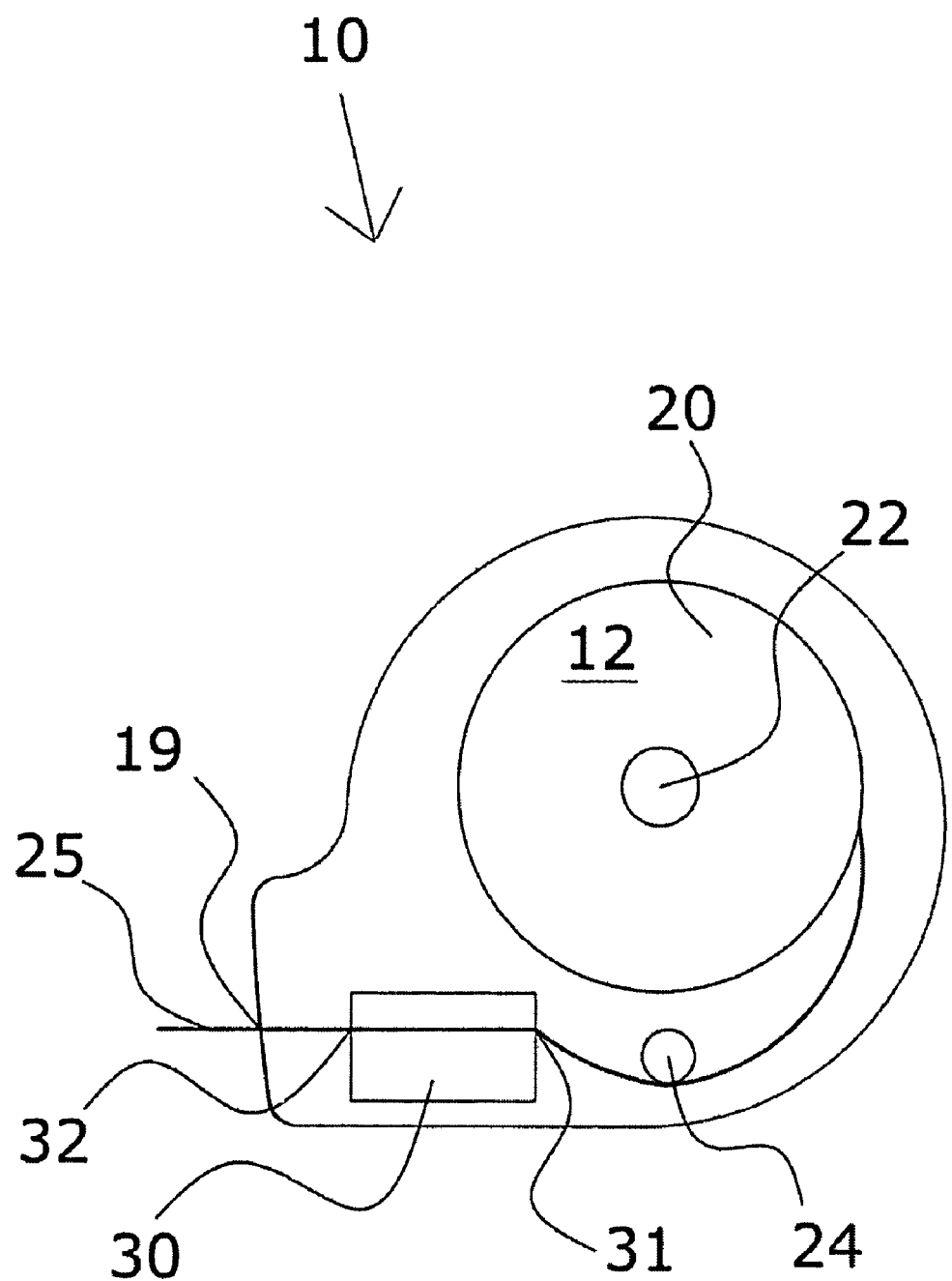
FIG. 2 is a top diagrammatic view of the first embodiment of the articulating paper dispenser of the present invention.

Referring now to FIG. 1 and FIG. 2, an articulating paper dispenser, shown generally as reference number 10, is illustrated in accordance with the first preferred embodiment of the present invention, configured as a manually-dispensing articulating paper dispenser. As shown, the articulating paper dispenser 10 includes an upper housing 12 and a lower housing 15 that are securely engaged to form both an interior lubricant container 30 for holding and covering the lubricant 33 and an interior spool-containing chamber 34. The spool-containing chamber is sized and configured to contain and store the articulating paper roll 22, as the articulating paper is dispensed.

The articulating paper dispenser 10 of the present invention is provided as both a disposable version and a refillable dispenser version.

To dispense, a strip of articulating paper (which has unwound from the articulating paper roll 20 inside the dispenser) is manually pulled from the articulating paper dispenser 10 through a dispensing slot 19. As strips of articulating paper 25 are dispensed, more paper is unwound from the articulating paper roll 20 and preferably proceeds through the following path: around a restraining roller 24, through an entrance wiper 31, into the lubricant container 30 (where it is covered with a lubricant), out of lubricant container 30 via an exit wiper 32, and out of articulating paper dispenser 10 via dispensing slot 19.

The articulating paper dispenser 10 is anticipated to be hand held, so the outer shape and size of upper housing 12 and lower housing 15 is designed with ergonomics in mind. Lower housing 15 is preferably unitarily molded at the time of manufacture with the following parts: the base section of lubricant container 30, dispensing slot 19, restraining roller 24, entrance wiper 31, exit wiper 32, and the base section of spool-containing chamber 34. Shaft 16 is preferably unitarily molded with lower housing 15, but may optionally be rotatably attached. Restraining roller 24 is preferably rotatably attached to lower housing 15.

Upper housing 12 is configured to securely engage lower housing 15, thereby forming a lid for the spool-containing chamber base and a leak-resistant lid for the lubricant container base. Preferably, for the refillable version of the articulating paper dispenser, the upper housing 12 is slidingly engaged with lower housing 15. Optionally, a latch (not shown) may be provided to secure the engagement. For the disposable version of the articulating paper dispenser, the upper housing 12 is preferably fixedly attached to lower housing 15 at the time of manufacture.

Any of the wide variety of available articulating papers as are known in the art may be used in the articulating paper dispenser 10. These would include, for example, articulating paper of a wide variety of widths and thicknesses that is formed from a variety of materials, such as paper, film, Mylar, or silk, and that is embedded, impregnated, or coated with one or more color pigments. Articulating paper roll 20 is preferably obtained in a web or roll format, which has been achieved by winding the articulating paper roll 20 onto spool 22, although it may be wound into a roll in some other fashion, such as without a spool 22.

Spool 22 is placed on shaft 16, which may support spool 22 in either a loosely supported manner, or, optionally, in a rotatable manner. If shaft 16 is rotatable, optional adapters (not shown) that slidingly engage on spool 22 to facilitate a snug fit between spool 22 and shaft 16 may be included, if desired.

The interior of upper housing 12 is configured to provide a leak-resistant lid for the lubricant container 30, securely closing the top of the lubricant container 30 when upper housing 12 is engaged on lower housing 15. The interior of upper housing 12 thus forms container lid 13, 14 to substantially enclose the lubricant located within lubricant container 30.

Restraining roller 24 aids in holding the articulating paper 25 in the proper position to enter lubricant container 30. The lubricant container 30 is configured to hold and to store a lubricant that, when applied to the strip of unwound articulating paper 25, will enable the articulating paper 25 to provide a more precise, accurate marking of occlusal contact points. Preferably the lubricant 33 (FIG. 5) contained in lubricant container 30 will be petroleum jelly sold under the trademark Vaseline, but may optionally be some other water-based or oil-based lubricant, such as lanolin, mineral oil, or glycerin.

The lubricant container 30 may be provided in any shape, such as rectangular (as shown) or circular. The side wall of lubricant container 30 is configured with an entrance wiper 31 and an exit wiper 32, which are slots or openings that are designed to allow the articulating paper 25 to enter and exit lubricant container 30 from the spool-containing chamber 34, while containing the lubricant 33 and preventing leakage. Therefore, entrance wiper 31 and exit wiper 32 should be sized only slightly larger than the articulating paper 25 or, alternatively, can be sized somewhat larger with a flexible gasket material (now shown) lining entrance wiper 31 and exit wiper 32 to aid in containment of the lubricant. Exit wiper 32 is configured to remove excess lubricant from articulating paper 25, leaving only a thin coating of lubricant remaining on either side of articulating paper 25 after it passes through exit wiper 32. After the lubricant-coated articulating paper 25 exits from the lubricant container 30 via exit wiper 32, it exits the articulating paper dispenser 10 via dispensing slot 19.

As the articulating paper 25 is dispensed from the articulating paper system, it is coated on both sides with a thin layer of the lubricant. The articulating paper 25 can be cut or torn to the appropriate length by the user. The lubricant-coated articulating paper is then used to check a patient's occlusion more accurately and precisely.

The disposable articulating paper dispenser 10 is pre-filled with the articulating paper roll 20 and with the lubricant 33 enclosed in lubricant container 30 at the time of manufacture. The disposable articulating paper dispenser 10 can be conveniently discarded when the last of the articulating paper roll 20 has been dispensed and then replaced with a new articulating paper dispenser 10.

Alternatively, the articulating paper dispenser 10 can be Configured as a refillable container. Thus it would open to enable the user to replace both the articulating paper roll 20 and the lubricant 33. To replace articulating paper roll 20, the user would insert the replacement articulating paper roll 20 onto shaft 16 and place an unwound length or section of the articulating paper 25 around restraining roller 24. The unwound section of the articulating paper 25 would then be threaded into entrance wiper 31, through lubricant container 30, into exit wiper 32, and out of articulating paper dispenser 10 via dispensing slot 19. A refillable articulating paper dispenser 10 would allow the user to reduce operating costs, while the disposable model offers more convenience.

Figure 3:
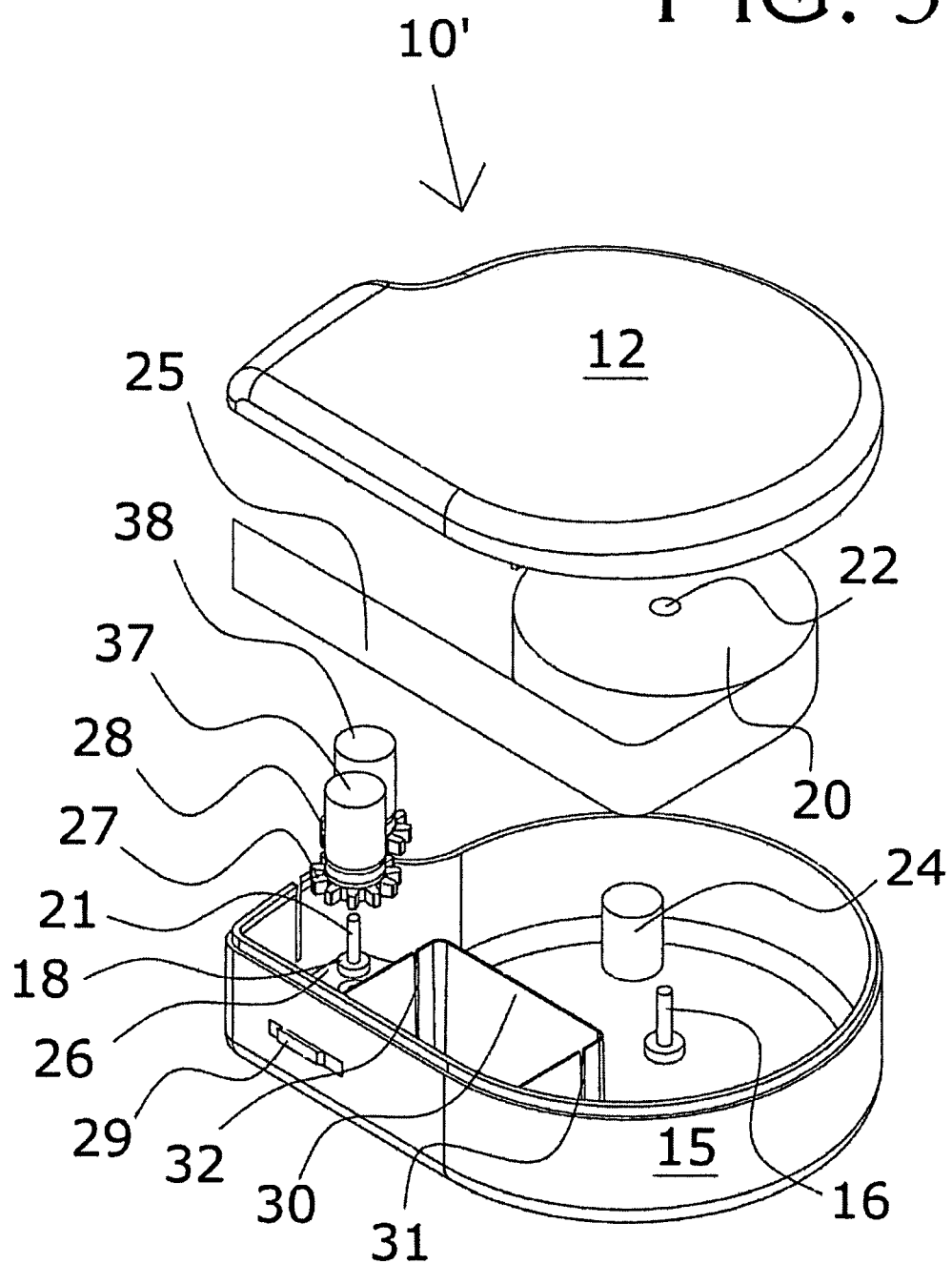
FIG. 3 is a perspective, expanded view showing a second preferred embodiment of the articulating paper dispenser of the present invention.
Figure 4:
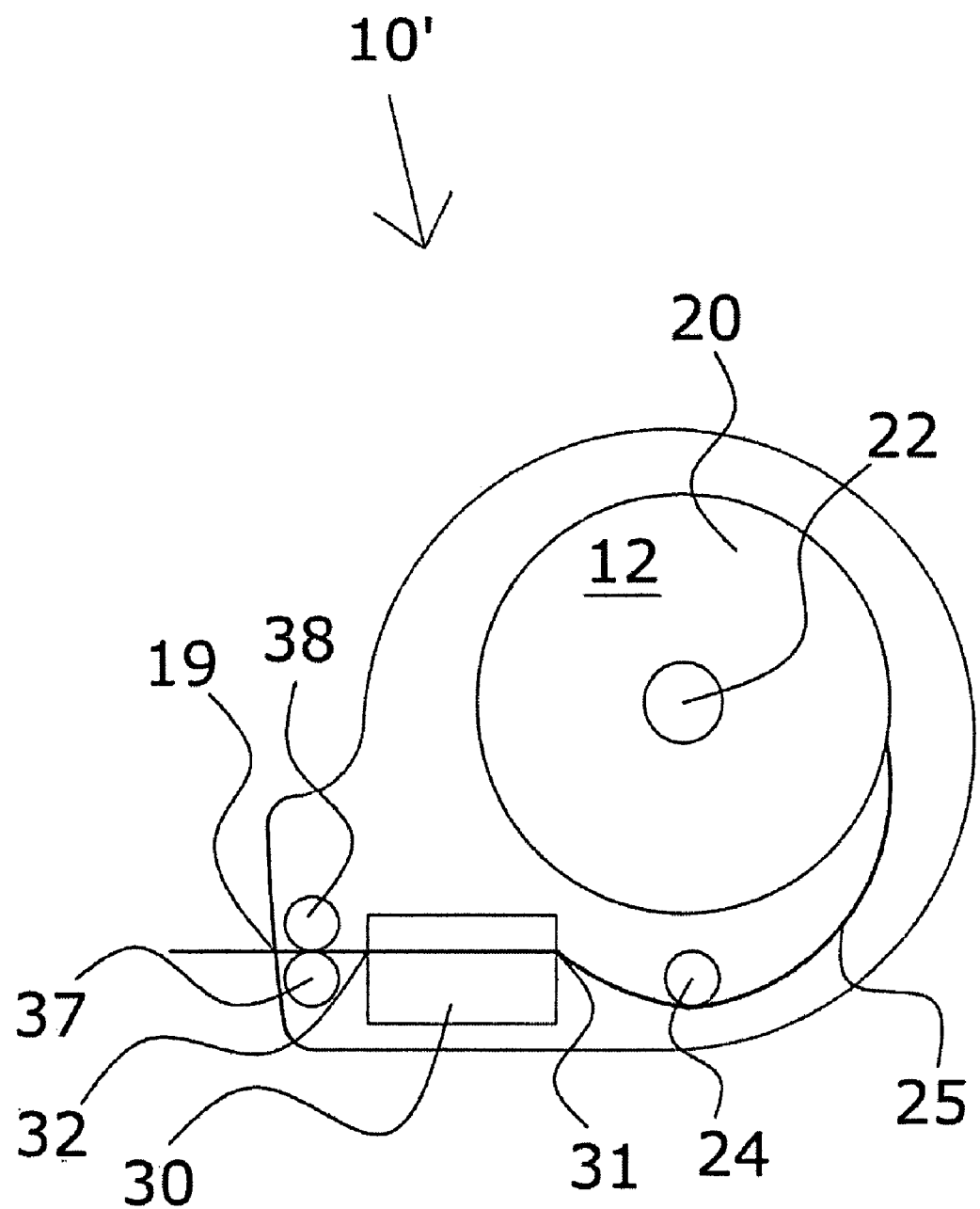
FIG. 4 is a top diagrammatic view of the second preferred embodiment of the articulating paper dispenser of the present invention.

Referring now to FIG. 3 and FIG. 4, a second preferred embodiment of the present invention is illustrated that is similar to the first embodiment of FIG. 1 and FIG. 2, but is configured as a motorized articulating paper dispenser 10'. The second embodiment is similar to the first embodiment with the addition of a battery-powered motor 26 (and its associated components) that provides power to unwind the strip of articulating paper 25 and to automatically extend it from dispensing slot 19.

Motor 26 provides power through bushing 18 to shaft 21 that is coupled to first gear 28. First gear 28 engages second gear 27. First pressure roller 38 and second pressure roller 37 are coupled to first gear 28 and second gear 27, respectively. Second pressure roller 37 is rotated counter-clockwise and pressure roller 38 is rotated clockwise either in contact with one another or with only the width of articulating paper 25 between them. Thus the articulating paper 25 is held between them and is automatically extended from dispensing slot 19. As the articulating paper 25 is drawn between first pressure roller 37 and second pressure roller 38, the articulating paper roll 20 is further unwound and the paper is drawn through the articulating paper path. One or more small batteries (not shown) are provided to power motor 26. Motor 26 is preferably provided with a manually activated on-off switch 29. A motor control system (not shown) is may optionally be supplied to control and to actuate motor 26 to dispense a selected length of the articulating paper. If desired, adjustable motor control system settings can be provided to set the dispensed length of articulating paper dispensed by the motor.

Figure 5:
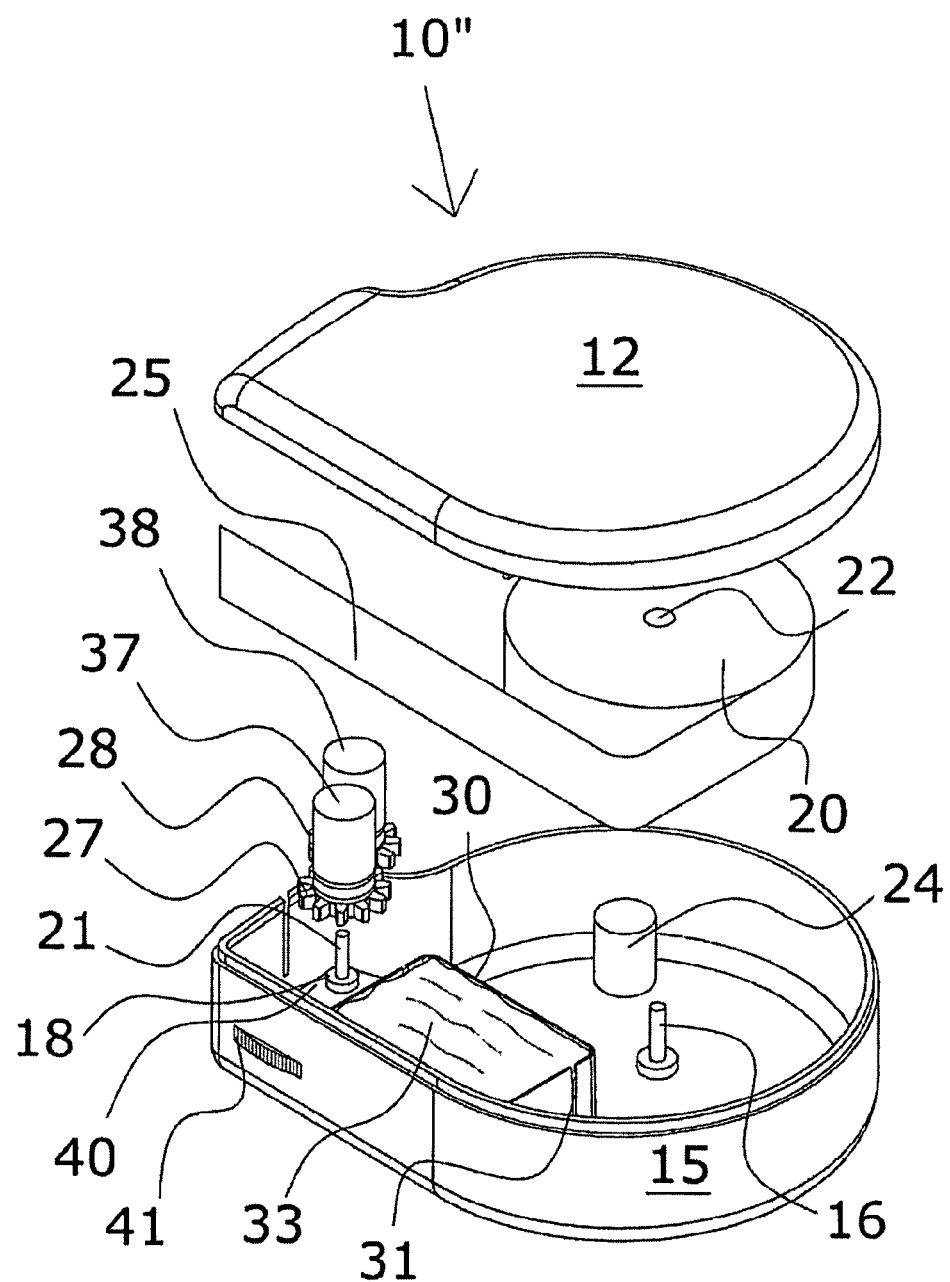
FIG. 5 is a perspective, expanded view showing a third embodiment of the articulating paper dispenser of the present invention.

Referring now to FIG. 5, a third preferred embodiment of the present invention is illustrated, configured as a mechanically activated articulating paper dispenser 10". The third embodiment is similar to the second embodiment but, instead of motor 26, it includes a manual power input device and appropriate mechanical linkages and gearing to utilize the manually input power to unwind the strip of articulating paper 25 and to extend it from dispensing slot 19. Such manual power input device may be, for example, a lever, or, as illustrated, a thumb wheel 41. Preferably the mechanical linkages and gearing are disposed within an enclosure or casing 40.

When thumb wheel 41 is moved laterally, it drives gearing in casing 40 that is coupled to first gear 28 via shaft 21 through bushing 18. First gear 28 engages second gear 27, thereby rotating second pressure roller 37 counter-clockwise and first pressure roller 38 clockwise with the articulating paper 25 between them. Thus moving thumb wheel 41 extends the articulating paper 25 from dispensing slot 19.

Other mechanically activated dispensing mechanisms as are known in the art, such as a spring action mechanism, could also be used.

The articulating paper dispenser is preferably molded from plastic materials or other synthetic or semi-synthetic polymers, for example: ABS resins, acetyl resins, nylon resins, urethane resins, or high impact polystyrene resins.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

I claim:

1. An articulating paper dispenser for lubricating and dispensing an unwound section of an articulating paper roll, comprising:
    an outer housing comprising an upper housing and a lower housing, wherein said upper housing is fittingly engagable on said lower housing, wherein said outer housing is sized and configured to receive said articulating paper roll, and wherein said lower housing comprises at least one lower housing side wall, and wherein said at least one lower housing side wall is configured with a dispensing slot that is configured for dispensing said unwound section of said articulating paper roll;
    a lubricant container firmly attached to said lower housing, said lubricant container having at least one lubricant container side wall in a configuration forming a lubricant reservoir to contain and deliver a lubricant;
    an entrance wiper slot provided through said at least one lubricant container side wall at a first location;
    an exit wiper slot provided through said at least one lubricant container side wall at a second location, wherein said entrance wiper slot and said exit wiper slot are positioned to guide said paper to pass directly through said lubricant reservoir;
    a flexible entrance wiper gasket material lining said entrance wiper slot, wherein said entrance wiper gasket material retains said lubricant within said lubricant reservoir, while allowing said paper to pass therethrough;
    a flexible exit wiper gasket material lining said exit wiper slot, wherein said exit wiper gasket material retains said lubricant within said lubricant reservoir, while allowing said paper to pass therethrough and removes excess lubricant from said paper, leaving only a thin coating of lubricant remaining on both sides of said paper;
    a restraining roller rotatably attached to said lower housing; and
    a shaft attached to said lower housing, said shaft sized to receive said articulating paper roll.

2. The articulating paper dispenser for lubricating and dispensing an unwound section of an articulating paper roll as recited in claim 1, further comprising:
    a drive means operably mounted within said lower housing; and
    a pair of pressure rollers disposed within said lower housing and operably coupled to said drive means, wherein said pair of pressure rollers are configured to extend a portion of said unwound section of said articulating paper roll through said dispensing slot when said drive means is activated.

3. The articulating paper dispenser for lubricating and dispensing an unwound section of an articulating paper roll, as recited in claim 2, wherein said drive means comprises a motor.

4. The articulating paper dispenser for lubricating and dispensing an unwound section of an articulating paper roll as recited in claim 2, wherein said drive means comprises a manual power input device.

5. The articulating paper dispenser for lubricating and dispensing an unwound section of an articulating paper roll as recited in claim 4, wherein said manual power input device comprises a thumb wheel.

6. The articulating paper dispenser for lubricating and dispensing an unwound section of an articulating paper roll as recited in claim 2, wherein said articulating paper roll is disposed on said shaft, and wherein said unwound section of said articulating paper extends from said articulating paper roll through said entrance wiper slot into said lubricant container and exits from said lubricant container through said exit wiper slot and extends through said dispensing slot to the exterior of said outer housing.

7. The articulating paper dispenser for lubricating and dispensing an unwound section of an articulating paper roll as recited in claim 2, further comprising a lubricant disposed within said lubricant container.

8. The articulating paper dispenser for lubricating and dispensing an unwound section of an articulating paper roll as recited in claim 7, wherein said lubricant comprises petroleum jelly.

9. A lubricating articulating paper dispenser for lubricating and dispensing an unwound strip of articulating paper from an articulating paper roll comprising:
   a lower housing having an interior bottom surface, said lower housing comprising a lubricant container base, a spool-containing chamber base, and at least one lower housing outer side wall, wherein said at least one lower housing outer side wall is configured with a dispensing slot, wherein said spool-containing chamber base is sized and configured to receive said articulating paper roll,
   said lubricant container comprising at least one lubricant container side wall in a configuration forming a lubricant reservoir to contain and deliver a lubricant;
   an entrance wiper slot provided through said at least one lubricant container side wall at a first location;
   an exit wiper slot provided through said at least one lubricant container side wall at a second location, wherein said entrance wiper slot and said exit wiper slot are positioned to guide said paper to pass directly through said lubricant reservoir;
   a flexible entrance wiper gasket material lining said entrance wiper slot, wherein said entrance wiper gasket material retains said lubricant within said lubricant reservoir, while allowing said paper to pass therethrough;
   a flexible exit wiper gasket material lining said exit wiper slot, wherein said exit wiper gasket material retains said lubricant within said lubricant reservoir, while allowing said paper to pass therethrough and removes excess lubricant from said paper, leaving only a thin coating of lubricant remaining on both sides of said paper;
   an upper housing having an upper housing interior surface, said upper housing comprising at least one upper housing side wall, said at least one upper housing side wall configured to securely engage said at least one lower housing outer side wall, said upper housing interior surface configured to form a lubricant container lid and a spool-containing chamber lid;
   wherein said lower housing further comprises a shaft attached to said interior bottom surface of said lower housing within said spool-containing chamber base, wherein said shaft is configured to receive and to support said articulating paper roll; and
   wherein said lower housing further comprises a restraining roller attached to said interior bottom surface of said lower housing within said spool-containing chamber base, wherein said restraining roller is configured to guide said unwound strip of articulating paper.

10. The articulating paper dispenser for dispensing an unwound strip of articulating paper from an articulating paper roll, as recited in claim 9, wherein said shaft is rotatably attached to said interior bottom surface of said lower housing.

11. The articulating paper dispenser for dispensing an unwound strip of articulating paper from an articulating paper roll, as recited in claim 9, wherein said lubricant container base contains a lubricant.

12. The articulating paper dispenser for dispensing an unwound strip of articulating paper from an articulating paper roll, as recited in claim 11, wherein said lubricant comprises petroleum jelly.

13. The articulating paper dispenser for dispensing an unwound strip of articulating paper from an articulating paper roll, as recited in claim 9, wherein said spool-containing chamber base contains said articulating paper roll, and wherein said unwound strip of articulating paper extends from said spool-containing chamber base through said entrance wiper slot into said lubricant container base and extends from said lubricant container base through said exit wiper slot.

14. The articulating paper dispenser for dispensing an unwound strip of articulating paper from an articulating paper roll, as recited in claim 13, wherein said unwound strip of articulating paper extends said exit wiper slot and further extends through said dispensing slot to the exterior of said articulating paper dispenser.

15. The articulating paper dispenser for dispensing an unwound strip of articulating paper from an articulating paper roll, as recited in claim 9, further comprising:
   a motor disposed within said lower housing; and
   a first pressure roller disposed within said lower housing and operably coupled to said motor.

16. The articulating paper dispenser for dispensing an unwound strip of articulating paper from an articulating paper roll, as recited in claim 15, further comprising:
   a first pressure gear coupled to said motor and coupled to said first pressure roller, wherein said first pressure gear transmits rotational force from said motor to said first pressure roller;
   a second pressure gear coupled to said first pressure gear; and
   a second pressure roller coupled to said second pressure gear, wherein said first pressure roller and said second pressure roller are configured to allow said unwound strip of articulating paper to be placed between them in such a position as to be extended by the rotational force of said motor.

17. The articulating paper dispenser for dispensing an unwound strip of articulating paper from an articulating paper roll, as recited in claim 9, further comprising:
   a manual power input device; and
   a first pressure roller disposed within said lower housing and rotated by said manual power input device.

18. The articulating paper dispenser for dispensing an unwound strip of articulating paper from an articulating paper roll, as recited in claim 17, further comprising:
   a first pressure gear coupled to said manual power input device and coupled to said first pressure roller, wherein said first pressure gear transmits rotational force from said manual power input device to said first pressure roller;
   a second pressure gear coupled to said first pressure gear; and
   a second pressure roller coupled to said second pressure gear, wherein said first pressure roller and said second pressure roller are configured to allow said unwound strip of articulating paper to be placed between them in such a position as to be extended by the rotational force of said manual power input device.

19. The articulating paper dispenser for dispensing an unwound strip of articulating paper from an articulating paper roll, as recited in claim 18, wherein said manual power input device is a thumb drive.

\* \* \* \* \*